United States Patent
Gibertoni

(12) 
(10) Patent No.: US 6,514,232 B1
(45) Date of Patent: Feb. 4, 2003

(54) VACUUM ADJUSTMENT VALVE, PARTICULARLY FOR THORACIC DRAINAGE DEVICES

(76) Inventor: Andrea Gibertoni, Via Luosi 68, 41037 Mirandola (IT)

( * ) Notice: Subject to any disclaimer, the term of this patent is extended or adjusted under 35 U.S.C. 154(b) by 108 days.

(21) Appl. No.: 09/589,164

(22) Filed: Jun. 8, 2000

(30) Foreign Application Priority Data

Jun. 10, 1999 (IT) ......................................... MI99A1297

(51) Int. Cl.[7] .......................... A61M 5/00; F16K 17/34; F16K 17/20
(52) U.S. Cl. .................. 604/247; 604/319; 604/48; 137/484.2; 137/484.4; 137/529; 137/543.15; 137/543.19; 137/540; 137/469
(58) Field of Search .................. 137/484.2, 484.4, 137/469, 529, 543.15, 543.19, 543.17, 540; 604/319, 48, 93.01, 246, 247, 256, 540, 541, 902

(56) References Cited

U.S. PATENT DOCUMENTS

| | | | | |
|---|---|---|---|---|
| 4,889,151 A | * | 12/1989 | Oten ...................... | 137/543.17 |
| 4,911,697 A | * | 3/1990 | Kerwin ...................... | 604/319 |
| 5,141,504 A | * | 8/1992 | Herweck et al. ............ | 604/319 |
| 5,174,327 A | * | 12/1992 | Truax et al. ................ | 137/469 |
| 5,203,372 A | * | 4/1993 | Freiler ......................... | 137/469 |
| 5,323,807 A | * | 6/1994 | Gauld et al. ........... | 123/543.15 |
| 5,531,712 A | | 7/1996 | Malcom et al. | |
| 5,807,358 A | | 9/1998 | Karwoski | |

FOREIGN PATENT DOCUMENTS

| | | | | |
|---|---|---|---|---|
| DE | 38 13 942 A1 | * | 11/1989 | ................. 137/529 |
| FR | 2 580 773 A1 | * | 10/1986 | ................. 137/540 |
| GB | 2 112 124 A | * | 7/1983 | ................. 123/540 |
| GB | 2 115 524 A | * | 9/1983 | ................. 137/540 |
| JP | 56014663 A | * | 2/1981 | ................. 137/529 |
| JP | 56042771 A | * | 4/1981 | ................. 137/469 |
| JP | 56073274 A | * | 6/1981 | ................. 137/529 |
| JP | 56160471 A | * | 12/1981 | ................. 137/529 |
| JP | 05170400 A | * | 7/1993 | ................. 137/469 |

* cited by examiner

*Primary Examiner*—Thomas Denion
*Assistant Examiner*—Thai-Ba Trieu
(74) *Attorney, Agent, or Firm*—Guido Modiano; Albert Josif; Daniel O'Byrne

(57) ABSTRACT

A vacuum adjustment valve, particularly for thoracic drainage devices, which comprises a valve body arranged in the air intake duct and tuning a first region connected to the intake duct and a second region connected to the drainage device. A regulator is arranged between the regions, is struck by the air stream and is operatively connected to a flow control element which controls a port for connection between the second region and an environment at atmospheric pressure. Adjustable elastic closure elements act on the flow control element.

7 Claims, 3 Drawing Sheets

VACUUM ADJUSTMENT VALVE, PARTICULARLY FOR THORACIC DRAINAGE DEVICES

BACKGROUND OF THE INVENTION

The present invention relates to a vacuum adjustment valve, particularly for thoracic drainage devices.

It is known that vacuum is used in many clinical situations in order to increase the effectiveness of drainage or, for example, to stabilize the position of the lungs in case of pneumothorax or pneumonotomy.

In all these situations the applied level of vacuum is to always be correctly controlled, both because it takes into account the clinical condition of the patient and most importantly because its uncontrolled increase can be considerably dangerous for the safety of the patient.

Vacuum in drainage devices is normally controlled by means of a so-called water seal valve having a water column arranged in parallel to the collection vessel that is connected to the patient; said solution is usually an integral part of the drainage system.

The continuous aspiration of air from the column indicates that the intended vacuum has been reached.

The height of the water column, typically between 10 and 20 centimeters, determines the intended level of vacuum.

Said valves are valid from a functional point of view, but they suffer the drawback that they are very noisy due to the continuous bubbling of air in the water column; this characteristic is particularly unpleasant for the patient especially at night, also since the drainage system remains connected to the patient for several days.

Another problem is constituted by the fact that by using the water seal valve, the drainage device must not be tipped, since the adjustment of the water column would otherwise be lost; moreover, in the water column valve the level of the water varies due to evaporation, with a consequent reduction in the applied vacuum.

In order to try to obviate these drawbacks, Italian patent No. 1293811 discloses a vacuum adjustment valve which is substantially constituted by a flexible tubular element associated with adjustable elastic means, and is interposed on the air intake duct.

The tubular element is connected to a plate having an opening which can hermetically engage an inlet which is connected to a drainage device.

The tubular element is surrounded by an environment at atmospheric pressure, so that when the degree of vacuum increases the tubular element is subjected both to radial contraction, which causes the compression of the spring, and to an axial thrust on the surface of the plate, so that automatic compensation occurs.

While the above solution is valid in many cases, it is however difficult to set and in particular it has not shown sufficiently uniform response; accordingly, it has failed to provide constant results.

SUMMARY OF THE INVENTION

The aim of the invention is to solve the above problem by providing a vacuum adjustment valve, particularly for thoracic drainage devices, which is particularly sensitive and is capable of providing at all times a uniform response which is a direct function of the intake air stream.

Within the scope of this aim, a particular object of the invention is to provide a valve which, in case of sudden increases in the level of vacuum, is capable of reacting in real time, producing an immediate reduction of the degree of vacuum, thus preventing transmission of suction level peak to the drainage device.

Another object of the present invention is to provide a valve which can operate in any position, can be easily set with optimum repeatability of its results, and is also able of giving the greatest assurances of reliability and safety in use.

Another object of the present invention is to provide a valve which can be easily obtained starting from commonly commercially available elements and materials and is competitive from a merely economical point of view.

These and other objects which will become better apparent hereinafter are achieved by a vacuum adjustment valve, particularly for thoracic drainage devices, according to the invention, characterized in that it comprises a valve body arranged in the air intake duct and forming a first region connected to said intake duct and a second region connected to a drainage device, a regulator being arranged between said regions, said regulator being struck by the air stream and being operatively connected to a flow control element which controls a port for connection between said second region and an environment at atmospheric pressure, adjustable elastic closure means acting on said flow control element.

BRIEF DESCRIPTION OF THE DRAWINGS

Further characteristics and advantages will become better apparent from the description of a preferred but not exclusive embodiment of a vacuum adjustment valve according to the invention, particularly for thoracic drainage devices, illustrated only by way of non-limitative example in the accompanying drawings, wherein.

DESCRIPTION OF THE PREFERRED EMBODIMENTS

Figure 1:
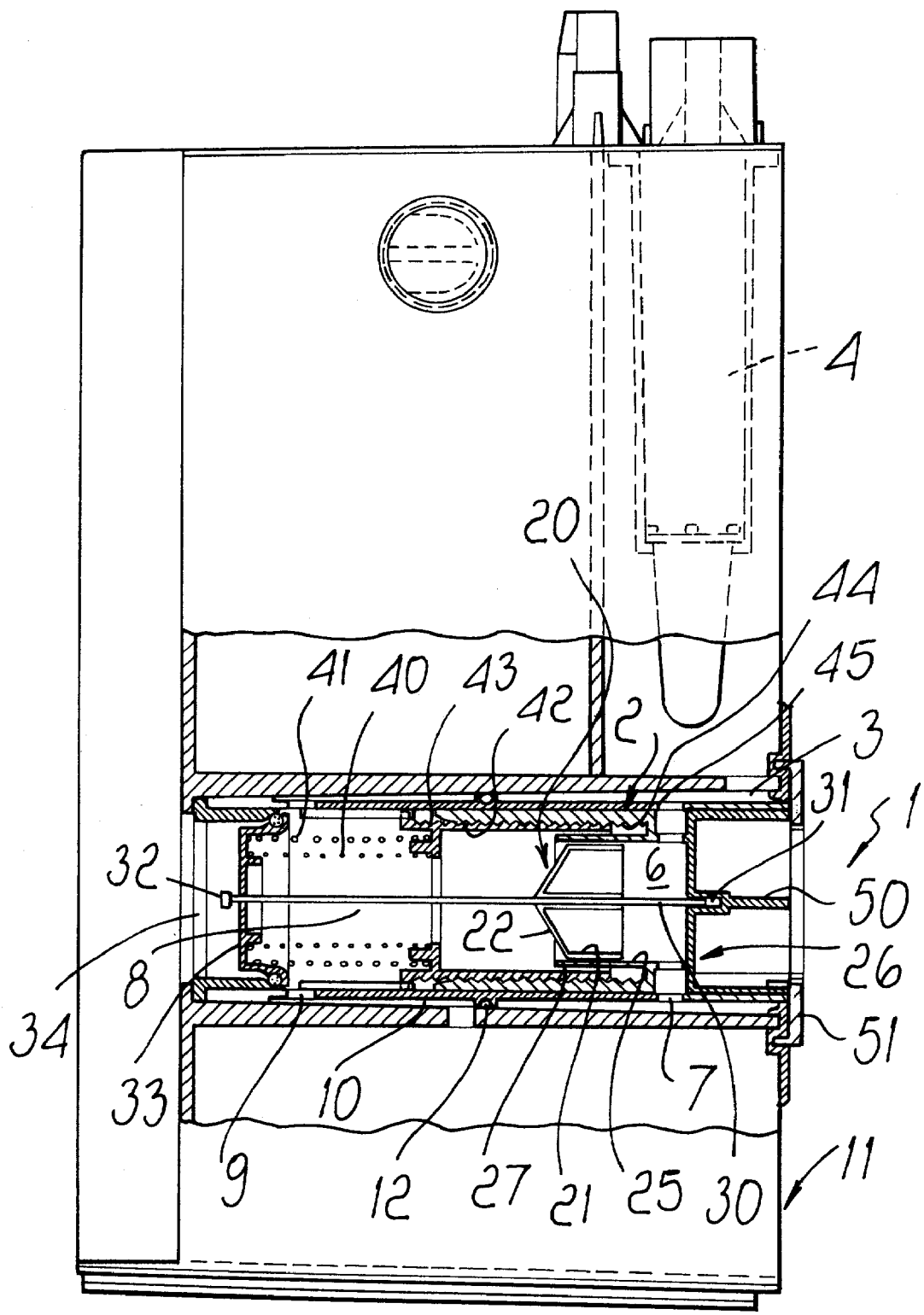
FIG. 1 is a schematic sectional view of the valve according to the invention, applied to a thoracic drainage device.
Figure 2:
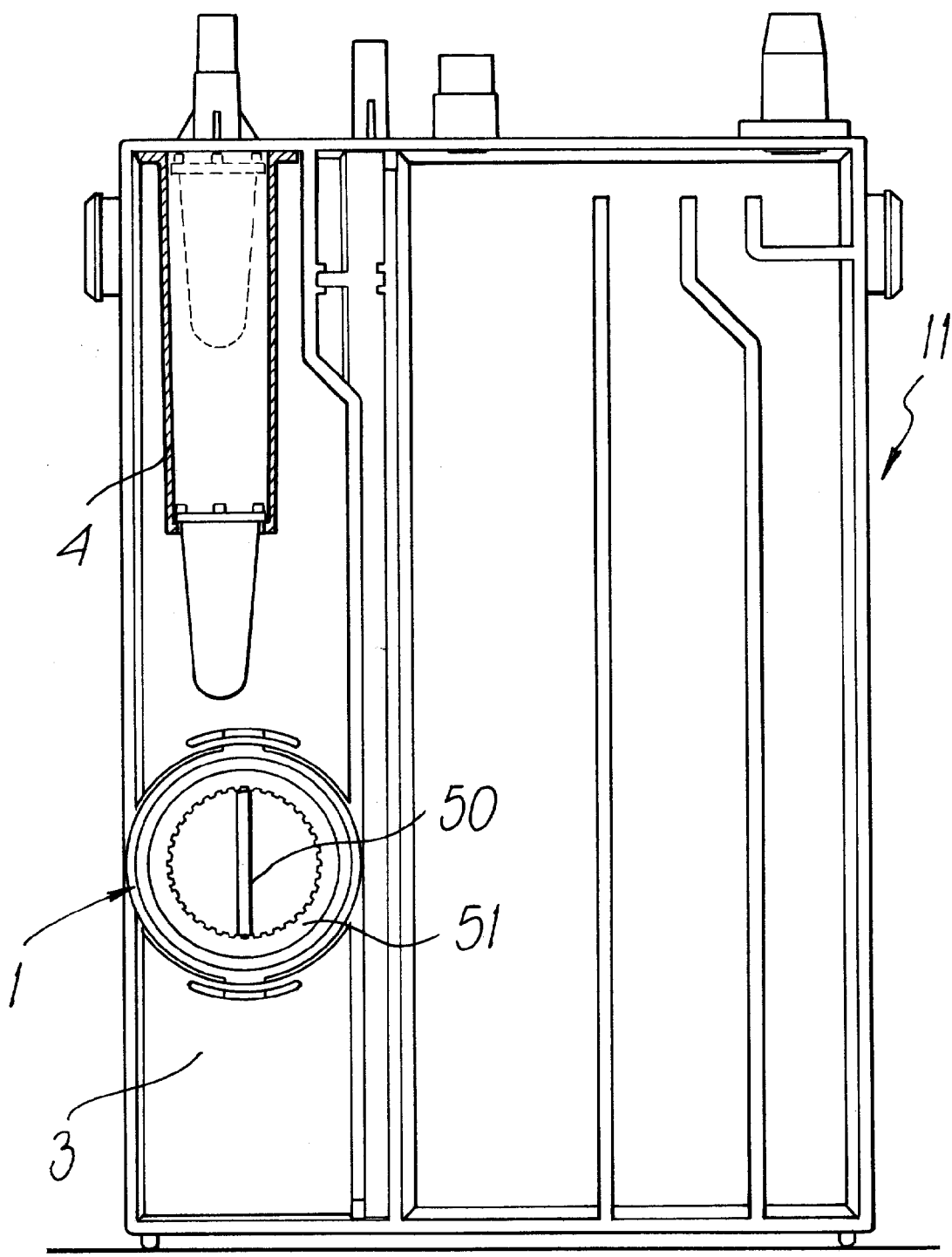
FIG. 2 is a front view of the valve inside a thoracic drainage device.
Figure 3:
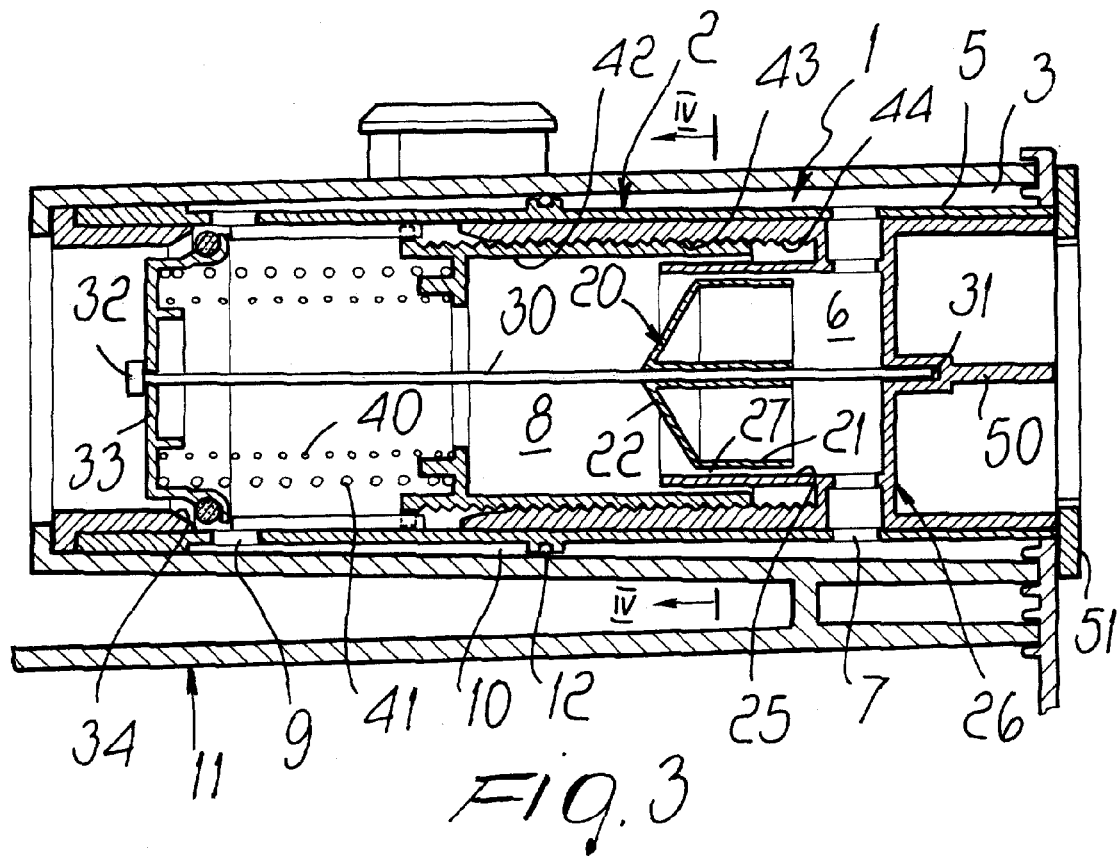
FIG. 3 is a sectional view of the valve with the flow control element in the open position, in case of a high level of suction inside the second region.
Figure 4:
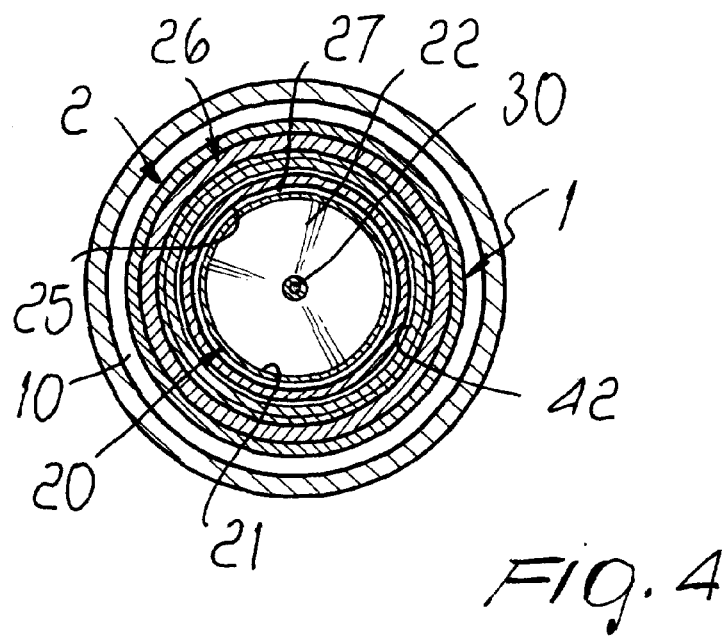
FIG. 4 is a sectional view, taken along the plane IV—IV of FIG. 3.

With reference to the figures, the vacuum adjustment valve particularly for thoracic drainage devices, according to the invention, generally designated by the reference numeral 1, comprises a valve body 2 which can be arranged in the air intake duct 3 in which there acts a conventional flowmeter 4, which indicates the level of suction. and a second region 8, which by means of an intake port 9 is connected to a coupling 10 for connection to the drainage device, generally designated by the reference numeral 11.

The separation between the coupling 10 and the duct 3 is provided by means of an O-ring 12.

Between the first region 6 and the second region 8 a regulator 20 is provided which has a cylindrical body 21 with a conical blending portion 22 directed toward the second region 8. The cylindrical body 21 forms, with the cylindrical side wall 25 of an adjustment element 26, an interspace 27 providing the passage of the air stream that peripherally strikes the regulator 20, which is supported by a shaft 30 accommodated, at one end, in a seat 31 formed by the adjustment element 26 and ends, at its other end, with a wider portion 32. The shaft 30 passes through a flow control element 33 which seals a port 34 for connection between the second region and a pressurized environment in which the wider portion 32 is arranged.

Adjustable elastic means act on the flow control element 33 and are preferably constituted by a first spring 40 and by a second spring 41 which act between the face of the flow control element 33 directed toward the second region and an adjustment sleeve 42 accommodated in the second region and peripherally provided with a male thread 43 engaging a female thread 44 of the adjustment element 26, which is turned so as to cause, in the sleeve 42, a translatory motion which varies the compression on the springs.

The adjustment element 26 advantageously has a diametrical knob 50 which acts as a grip element and as an element for visually indicating the set adjustment level in alignment with a frontally provided ring 51.

The vacuum adjustment valve according to the invention is particularly sensitive, since it is the entrainment action of the air stream applied to the regulator 20 that causes the translatory motion of said regulator and, if a preset level is exceeded, is capable of overcoming the contrast applied by the springs 40 and 41, accordingly achieving a normally limited opening of the flow control element 33 with the normal passage of air and, in case of sudden suction peaks, a sudden opening by a relatively large extent, which causes an immediate drop in the suction value, accordingly protecting the patient.

The particular structure according to the invention, which is based on creating an entrainment of the regulator 20 by the air stream, said entrainment increasing as the air stream that strikes the regulator increases, allows to have a constant response which is not subject to friction and can be set easily by adjusting the precompression of the setting springs.

The invention thus conceived is susceptible of numerous modifications and variations, all of which are within the scope of the appended claims.

All the details may furthermore be replaced with other technically equivalent elements.

In practice, the materials used, as well as the contingent shapes and dimensions, may be any according to requirements.

The disclosures in Italian Patent Application No. MI99A001297 from which this application claims priority are incorporated herein by reference.

What is claimed is:

1. A vacuum adjustment valve, particularly for thoracic drainage devices, comprising: an intake duct; a drainage device; a flow control element, a valve body arranged in said air intake duct and forming a first region, which is connected to said intake duct, and a second region, connected to said drainage device; a port for connecting said second region to an environment at atmospheric pressure; a regulator being arranged between said two regions, said regulator being provided so as to be struck by an air stream and being operatively connected to said flow control element which controls said port; and adjustable elastic closure means acting on said flow control element.

2. The valve of claim 1, further comprising: an intake port; a coupling for connection to the drainage device; and a gasket for hermetic separation between said coupling and said intake duct; said valve body having an outer enclosure which internally forms said first region and is connected to said intake duct, said second region being formed inside said outer enclosure and being connected, by way of said intake port, to said coupling.

3. The valve of claim 2, comprising an adjustment element, said regulator having a cylindrical body with a conical blending portion which is directed toward said second region, said cylindrical body being accommodated inside the cylindrical side wall of an adjustment element in order to form an interspace having a preset cross-section for passage of the air stream.

4. The valve of claim 3, further comprising a shaft which is connected to said regulator and is accommodated, at a first end, in a seat which is formed in a bottom part of said cylindrical side wall, said shaft having at a second end thereof, a wider portion which is located in a portion of said flow control element that is directed toward said environment at atmospheric pressure, said shaft being arranged so as to pass hermetically through said flow control element.

5. The valve of claim 4, comprising an adjustment sleeve accommodated in said second region and connected, by way of a male thread thereof, to a female thread formed at the adjustment element provided with said cylindrical side wall, said adjustable elastic closure means acting between said flow control element and said adjustment sleeve.

6. The valve of claim 5, wherein said adjustable elastic closure means comprise concentric springs.

7. The valve of claim 5, comprising a ring which is fixed on said drainage device, said adjustment element having a diametrical knob which is adapted to act as a grip element and as an element for displaying a set adjustment value by alignment with said ring.

* * * * *